US00PP37294P2

(12) United States Plant Patent
Espín

(10) Patent No.: US PP37,294 P2
(45) Date of Patent: Mar. 3, 2026

(54) GRAPEVINE PLANT NAMED 'BLOMG04'

(50) Latin Name: *Vitis vinifera*
Varietal Denomination: BLOMG04

(71) Applicant: BLOOM FRESH INTERNATIONAL LIMITED, London (GB)

(72) Inventor: Juan Carreño Espín, Murcia (ES)

(73) Assignee: BLOOM FRESH INTERNATIONAL LIMITED, London (GB)

( * ) Notice: Subject to any disclaimer, the term of this patent is extended or adjusted under 35 U.S.C. 154(b) by 0 days.

(21) Appl. No.: 19/219,576

(22) Filed: May 27, 2025

(51) Int. Cl.
*A01H 6/88* (2018.01)
*A01H 5/08* (2018.01)

(52) U.S. Cl.
USPC ..... Plt./205

(58) Field of Classification Search
USPC ..... Plt./205
CPC ..... A01H 6/88; A01H 5/08
See application file for complete search history.

(56) References Cited

U.S. PATENT DOCUMENTS

PP33,387 P2 8/2021 Martinez et al.

*Primary Examiner* — Keith O. Robinson
(74) *Attorney, Agent, or Firm* — Michael Best & Friedrich LLP

(57) ABSTRACT

'BLOMG04' is a new and distinct grapevine plant with novel characteristics that include good fertility and excellent neutral flavor with a good balance between sugar-acid. The berries produced by 'BLOMG04' are violet (5RP4/2), with colored flesh (5R3/4), and crunchy texture. The berries produced by 'BLOMG04' are large, weighing 6.5 g/berry on average, and harvested in late August in Murcia, Spain.

1 Drawing Sheet

Latin name of the genus and species: *Vitis vinifera.*
Cultivar denomination: 'BLOMG04'.

CROSS-REFERENCE TO RELATED APPLICATIONS

This application is related to Spanish National Listing no. 20240244, filed Oct. 15, 2024, European Union Plant Breeders Rights Application No. 2024/2402, filed Nov. 5, 2025, and European Union Reference Listing No. 2244015, filed Nov. 4, 2024.

BACKGROUND

Described herein is a new and distinct variety of seedless grapevine named 'BLOMG04'. The variety originated from a hybridization performed in Murcia, Spain during 2018 between 'ITUMNINE' (U.S. Plant Pat. No. 33,387), as the pollen parent, and '15M-121-511' (unpatented), as the seed parent. Abortive seed traces were embryo cultured, and the resulting plant was planted in an evaluation block during 2019. The first evaluation of the fruit produced by 'BLOMG04' was performed during 2020. 'BLOMG04' was first asexually propagated by field grafting dormant hardwood scions to 1103 Paulsen rootstock (not patented) in 2021 in Murcia, Spain. Fruit from the resulting six grafted 'BLOMG04' vines was first harvested in 2022. All characteristics and distinctions remain true to form and are established and transmitted through succeeding propagations.

SUMMARY

The following are the most outstanding and distinguishing characteristics of 'BLOMG04'. 'BLOMG04' produces naturally large (6.5 g/berry) seedless violet (5RP3/2) berries, with colored flesh (5R3/4), a crunchy and firm texture, a cylindrical shape, with an excellent neutral flavor with a good balance between sugar-acid neutral, and a high fertility index (1.3), that are harvested in late August, in Murcia, Spain.

'BLOMG04' is believed to be most similar to 'Blagratwo' (not patented). Nonetheless, the new cultivar can be distinguished from 'Blagratwo' based at least upon berry shape, berry flesh color and berry skin color. The berries produced by 'BLOMG04' have a cylindrical shape while the berries produced by 'Blagratwo' have an obovoid shape; and the berries of 'BLOMG04' are violet and have coloured flesh while the berries of 'Blagratwo' are blue black and the flesh is not pigmented.

'BLOMG04' can be distinguished from its male parent, 'ITHUMNINE' (U.S. Plant Pat. No. 33,387), in that the new cultivar produces berries with colored flesh while the berries produced by 'ITHUMNINE' do not have pigmented flesh. The berry skin of 'BLOMG04' is thinner than that of 'ITHUMNINE'.

'BLOMG04' can be distinguished from its female parent, '15M-121-511' (unpatented), in that the new cultivar, 'BLOMG04', produces seedless grapes while '15M-121-511' produces seeded grapes. The bunches produced by 'BLOMG04' are heavier than the bunches produced by '15M-121-511'. The berries of 'BLOMG04' have a crunchy and firm texture where the berries of '15M-121-511' have a soft texture.

BRIEF DESCRIPTION OF THE DRAWING OR PHOTOGRAPH

The accompanying color photograph illustrates the overall appearance of the 'BLOMG04' grapevine plant showing the colors as true as it is reasonably possible to obtain in colored reproductions of this type. Colors in the photographs may differ slightly from the color values cited in the detailed botanical description that accurately describe the colors of the plant described herein. These figures are exemplary will vary depending on the plant and distinguishing characteristics.

FIG. 1 shows the form, foliage, and fruit of a 4-year-old 'BLOMG04' grapevine plant grown in the field at Murcia, Spain. FIG. 1 shows, from the top in a clockwise direction: mature upper surface leaf, immature upper surface leaf, inflorescence, longitudinal section of immature fruits, side view of immature fruits, longitudinal section of mature fruits, side view of mature fruits, a secondary fruit bunch (middle), a cutting of a young shoot with tendrils and leaves, and a primary fruit bunch. The colors shown are as true as can be reasonably obtained by conventional photographic procedures.

DETAILED BOTANICAL DESCRIPTION

The following detailed description sets forth the distinctive characteristics of 'BLOMG04'. The detailed description was obtained between March and November using 4-year-old plants grown in the field in Murcia, Spain. The color references are to the Munsell Plant Tissue Color Book, 2012 Edition by Munsell Color.

Classification:

*Family*.—Vitaceae.
*Botanical*.—*Vitis vinifera*.
*Common name*.—Grapevine.
*Cultivar name*.—'BLOMG04'.

Plant

*Plant habit and growth*.—Semi-erect.
*Age at maturity*.—4 years old.
*Size* (*at maturity*).—Height: 225 cm. Width: 300 cm.
*Vigor*.—Medium.
*Productivity*.—Medium, 1.3 fertility index, around 35 kg/plant and 14 t/acre.
*Rootstock*.—Name of rootstock: 1103 Paulsen Rootstock (not patented). Age of rootstock at time of grafting: one year old.

Trunk:

*Size*.—Diameter — 6.25 cm. Height (at measured diameter of 4 cm) — 45 cm above the ground.
*Shape*.—straight and cylindrical.
*Surface texture*.—Smooth, thin strips of peeling.
*Bark color*.—Interior — 5YR4/2. Exterior — 5YR4/6.

Canes:

*Size*.—Diameter — 7.3 mm. Length — 116 cm.
*Surface texture*.—Mature cane — smooth. Immature cane-very smooth and very finely ribbed.
*Form* (*woody shoot cross section form*).—Circular; pith in center with diaphragm at nodes.
*Color*.—Mature — 5 months, 5GY6/8 (anthocyanin 5R3/4). Immature — 4 weeks, 2.5GY6/8.
*Dorsal side of internodes*.—5GY6/8 (anthocyanins 5R3/4).
*Ventral side of internodes*.—5GY6/8 (anthocyanins 5R3/4).
*Dorsal side of nodes*.—5GY6/8.
*Ventral side of nodes*.—5GY6/8.
*Internode length* (*upper mature sun cane*).—10.9 cm.
*Internode width* (*upper mature sun cane*).—7.4 mm.
*Node width*.—12.8 mm.

Bud:

*Bud description*.—Winter bud — pointed, color 5YR5/4. Green bud — rounded, pointed, color 5GY7/8 with anthocyanins 2.5R5/6.
*Time of bud burst*.—26 March.
*Time of bud leaf burst*.—29 March.

Tendrils:

*Form*.—Mostly trifid and bifid.
*Size*.—Medium.
*Length*.—17.4 cm.
*Diameter*.—2.25 cm.
*Texture and distribution*.—Smooth, discontinuous, 0000000000010010010010110010 (0 means no tendril at that node and 1 means there is tendril at the node).
*Color*.—Mature — 4 weeks, 5GY6/8. Immature — 10 days, 5GY7/8.
*Anthocyanin*.—Mature — absent. Immature — absent.

Growing tips (young shoot):

*Pubescence*.—Absent.
*Color*.—5GY5/10.
*Anthocyanin*.—2.5R5/10; piping distribution, low intensity.
*Shape*.—Fully open.
*Apex*.—Triangular.
*Form of tip*.—Fully open.
*Shoot attitude before tying*.—Semi-erect.

Leaves:

*Shape*.—Pentagonal.
*Density*.—Medium.
*Apex*.—Pointed.
*Base*.—Pentagonal.
*Number of lobes*.—5.
*Depth of upper lateral sinuses of mature leaves*.—Medium.
*Arrangement of lobes of upper lateral sinuses on mature leaves*.—Slightly overlapped.
*Margin*.—Irregular teeth.
*Length of teeth on margin*.—2 to 15 mm.
*Shape of teeth on margin*.—Both sides convex.
*Texture* (*mature leaf*).—Upper surface-smooth, without goffering or blistering on upper side of blade. Lower surface-smooth, low density of prostrate hairs between main veins on lower side of blade.
*Size*.—Immature: Length — 7.3 cm, 10 days. Width — 7.5 cm, 10 days. Mature: Length — 18.42 cm, 4 weeks. Width — 17.6 cm, 4 weeks. Ratio of length/width of teeth (mature leaf) — 0.96.
*Color*.—Immature leaf: Upper surface — 5GY4/8 (anthocyanins 10R4/6). Lower surface — 5GY5/8. Mature leaf.—Upper surface — 7.5GY4/4. Lower surface — 5GY5/6. Autumn coloration: Upper surface — 5GY5/8 (anthocyanins 5R3/2). Lower surface — 5GY6/6 (anthocyanins 5R3/6).
*Venation*.—Pattern — palmate (veins on upper leaf are flat; veins on lower leaf are raised), without anthocyanins coloration. Length of middle vein in mature leaves — 12.5 cm.
*Color*.—Upper surface — 2.5GY8/8. Lower surface — 2.5GY8/6.
*Petiolar sinus*.—Brace-shaped, not limited by veins.
*Petiole*.—Length — 11.66 cm. Diameter — 2.74 mm. Color — 5GY6/6 (anthocyanin 2.5R6/6).

Floral cluster:

*General description and location*.—Mostly 3rd node; 100% with shoulders.

*Quantity of inflorescences per cluster*.—2000.

*Size*.—Length — 13.25 cm. Width — 7.75 cm hanging; 15.125 cm shoulders spread.

*Peduncle*.—Length — 5.5 cm.

*Inflorescences*.—Hermaphroditic.

*Stamens*.—5 per flower, straight, 3.25 mm.

*Anthers*.—Small, non-descript.

*Date of bloom*.—Start 26 April; 50%-2 May, 100%-8 May.

*Pollen amount*.—Abundant.

*Pollen color*.—5Y8/10.

*Calyptra*.—5 segments, complete separation.

*Calyptra color*.—5GY4/8.

Fruit:

*Time of year of commercial harvest and shipment*.—Late season, 20 August, in Murcia, Spain.

*Time of beginning of berry ripening*.—Late.

*Keeping quality*.—After 30 days of refrigerated conservation, the main and secondary stem remain hydrated. The berries keep its excellent flavor and crispness.

*Cluster* (*primary bunches*).—General size — large, 900 g. Length (without peduncle) — 19 cm (25 cm without tipping). Width — hanging 15.25 cm; shoulders spread 30.3 cm. Density — lax. Peduncle length — 5.6 cm. Peduncle diameter — 5.75 mm. Peduncle color — 2.5GY6/6. Number of berries per cluster — 130 tipped; 180 not tipped.

*Berry*.—Size — large, 6.5 g. Diameter — 18.4 mm. Length — 28.5 mm. Shape — cylindrical. Uniformity — very uniform. Brix content — 22.5° Brix. Titratable acidity — 0.41. Skin color (without bloom) — 5RP3/2. Skin color (with bloom) — 5RP4/2.

*Pedicel*.—Length — 6.5 mm. Diameter — 1.6 mm. Color — 2.5GY6/6. Strength of attachment to berry — strong.

*Cluster* (*secondary bunches*).—General size — small, 35 g. Length (without peduncle) — 7.5 cm. Width — hanging 8.6 cm; 10.8 cm shoulders spread. Density — medium. Peduncle: Length — 7.4 cm. Diameter — 2.8 mm. Color — 2.5GY6/6. Number of berries per cluster — 36 berries.

*Berry*.—Size — medium, 4 g. Diameter — 16.4 mm. Length — 22.9 mm. Shape — cylindrical. Uniformity — very uniform. Brix content — 19.3° Brix. Titratable acidity — 0.41. Skin color (without bloom) — 5RP3/2. Skin color (with bloom) — 5RP4/2. Pedicel: Length — 5.8 mm. Diameter — 1.3 mm. Color — 2.5GY6/6. Strength of attachment to berry — strong.

Berry flesh:

*Color*.—5R3/4.

*Juice, color*.—5R3/6.

*Juice production*.—Medium-high, 37.85%.

*Thickness of skin*.—Very thin.

*Flavor*.—Neutral, good balance sugar-acid.

*Fragrance*.—Neutral.

*Texture*.—Crunchy and firm.

*Seeds*.—Rudimentary, not detectable.

*Use*.—Table grape.

Disease and insect resistance: This cultivar is susceptible to the main diseases of its species, such as *Erysiphe necator, Plasmopara viticola, Botrytis cinerea, Daktulosphaira vitifoliae, Ceratitis capitata, Planococcus ficus, Planococcus citri*, and *Empoasca vitis*.

What is claimed:

1. A new and distinct variety of grapevine plant named 'BLOMG04' as substantially described and illustrated herein.

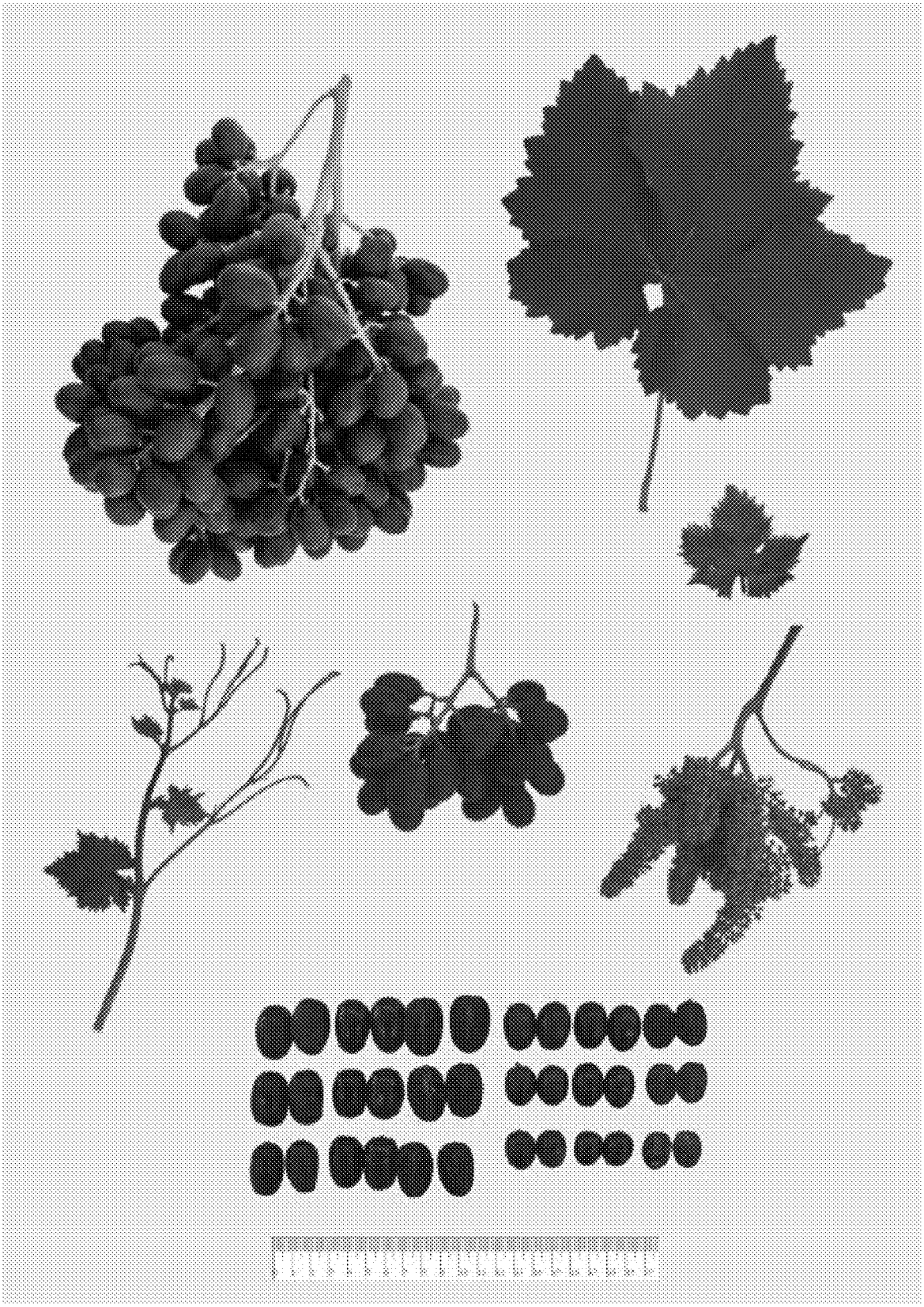

* * * * *